(12) United States Patent
Meulink

(10) Patent No.: US 6,863,692 B2
(45) Date of Patent: Mar. 8, 2005

(54) IMPLANT SLEEVE AND METHOD

(75) Inventor: Steven L. Meulink, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/294,134

(22) Filed: Nov. 14, 2002

(65) Prior Publication Data

US 2004/0098134 A1 May 20, 2004

(51) Int. Cl.⁷ .................................................. A61F 2/28
(52) U.S. Cl. ................ 623/23.52; 623/23.11; 606/76; 206/438; 206/363; 604/171
(58) Field of Search ................ 623/22.12, 22.46, 623/22.33, 23.23, 23.52; 606/76; 206/438, 363–370; 604/171, 172

(56) References Cited

U.S. PATENT DOCUMENTS

| | | | | |
|---|---|---|---|---|
| 3,818,514 A | * | 6/1974 | Clark | 623/22.12 |
| 4,064,567 A | * | 12/1977 | Burstein et al. | 623/23.46 |
| 4,728,335 A | * | 3/1988 | Jurgutis | 623/23.23 |
| 4,921,500 A | * | 5/1990 | Averill et al. | 623/22.45 |
| 5,308,673 A | * | 5/1994 | Tochacek et al. | 428/102 |
| 6,287,291 B1 | * | 9/2001 | Bigus et al. | 604/523 |

* cited by examiner

*Primary Examiner*—Corrine McDermott
*Assistant Examiner*—Kamrin Landrem
(74) *Attorney, Agent, or Firm*—Cary R. Reeves; Jonathan Feuchtwang

(57) ABSTRACT

Several embodiments of an implant sleeve are shown for use with implants inserted through a wound into a surgical site. In some embodiments, the sleeve is useful to protect mating implant components from contamination during insertion through the wound. In other embodiments, the sleeve is useful to clean components that have become contaminated during insertion.

21 Claims, 4 Drawing Sheets

IMPLANT SLEEVE AND METHOD

FIELD OF THE INVENTION

The present invention relates to sleeves for orthopaedic implants and their method of use.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

Several illustrative embodiments of an implant sleeve are described for use with implants inserted through a wound into a surgical site. In some embodiments, the sleeve is useful to protect mating implant components from contamination during insertion through the wound. In other embodiments, the sleeve is useful to clean components that have become contaminated during insertion. The components include mating surfaces of mechanical assemblies for joining multiple implant components together. The sleeve prevents or removes contamination that would interfere with the secure joining of the components. The mating components also include cemented anchoring surfaces to be inserted into a mass of cement placed at the surgical site or bone growth anchoring surfaces to be pressed against the bone to receive bone growth. The sleeve prevents or removes contamination that would interfere with the secure adhesion of the cement to the components or that would interfere with bone growth. The sleeve of the present invention is useful in a variety of surgical situations where delivering at least a portion of an implant to a surgical site free from wound contamination is desired. It is particularly useful where implantation is conducted through a small incision, as in minimally invasive surgery. With a small incision, is it more likely that implant surfaces will contact the soft tissues and fluids around the surgical wound and become contaminated.

Figure 1:
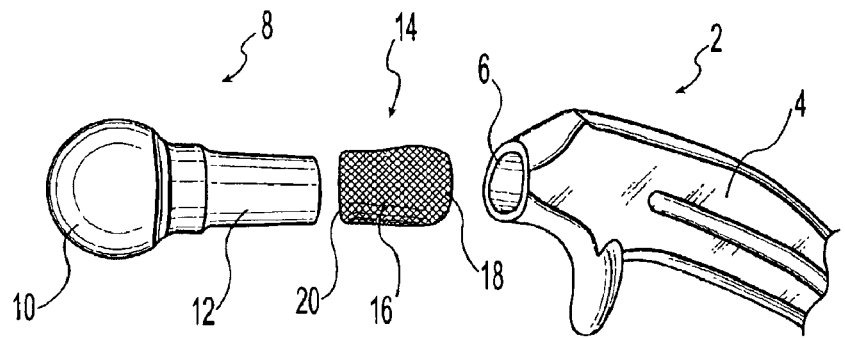
FIG. 1 is an exploded perspective view of an illustrative embodiment of a sleeve according to the present invention shown with modular implant components.
Figure 2:
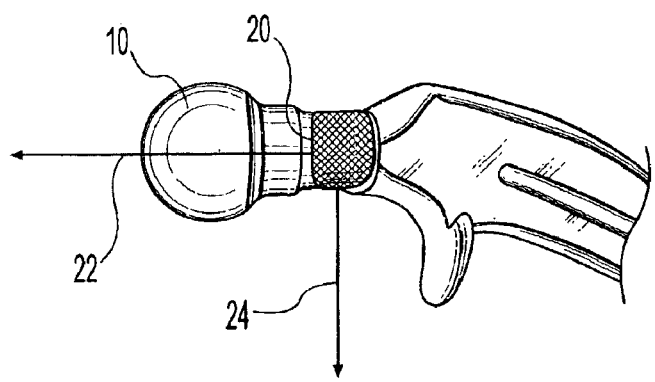
FIG. 2 is a perspective view of the sleeve of FIG. 1 assembled with the components of FIG. 1.

FIGS. 1 and 2 show an illustrative embodiment of a sleeve for an implant. Then implant includes a hip stem 2 having a shaft 4 for insertion into the intramedullary canal of a femur and a female taper 6 having an internal taper engaging surface for receiving a modular head and neck 8 for articulation with an acetabulum. The modular head and neck 8 has a smooth articulating head 10 and a male taper 12 having an external taper engaging surface. The male taper is received by the female taper 6 with their engaging surfaces in overlying engagement. The illustrative tapers 6, 12 form a locking junction that can be locked by impacting them together. The sleeve 14 includes a sidewall 16 forming a hollow cylinder with opposite open ends 18, 20. The sleeve 14 can be made from a variety of materials. In the illustrative embodiment, it is shown as a woven or knit, absorbent fabric than can be fit over the male taper 12 similar to a sock. The structure of the fabric allows it to stretch to fit over the male taper 12 in close-fitting relationship. The fabric can be made from any suitable natural or synthetic fiber. Other materials can be substituted for the woven fabric shown such as a non-woven fibrous sheet, a polymer film, a foil, a laminate, or other suitable materials. The sleeve 14 can stretch to allow its removal or it may be made with a frangible portion to break and separate as it is pulled away from the taper. One end 18 of the sleeve 14 may also be closed to protect the end of the male taper 12. If the end 18 is closed, it can be made with a frangible portion so that it will come open upon removal to facilitate removal of the sleeve 14. A frangible portion for a sleeve can be made in several ways, including using a materially that is inherently thin enough or weak enough to break when it is pulled such as a loosely twisted fibrous material or a thin film. A frangible portion can also be made by partially cutting through a portion of the sleeve or heat crimping a portion of the sleeve. The sleeve can be made to be frangible generally, or at a specific location.

In use, the sleeve 14 is slipped over the male taper 12 to cover at least a portion of the taper. The at least partially covered taper 12 is then placed near the female taper 6. The sleeve is gripped by one end 20 and pulled from the male taper 12. The tapers are then impacted and locked together. A head and neck 8 having a male taper 12 and a stem 2 having a female taper 6 are shown. The inventive sleeve 14 will work equally well with a head having a female taper and a stem having a male taper.

In one embodiment, the partially covered taper 12 is loosely inserted into the female taper 6 with the sleeve 14 positioned between the overlying taper engaging surfaces. Prior to locking the tapers 6, 12 together, the sleeve is gripped by one end 20 and pulled 22 from between the tapers to wipe the taper surfaces clean just before the tapers are locked together. The sleeve 14 can be gripped with a pair of forceps at one end 20 and pulled away from the hip stem 2. As the sleeve 14 is pulled from between the mating tapers, it is able to stretch further to go over the articulating head 10. Alternatively the sleeve can be made to break to allow it to be removed. The sleeve can also be removed by gripping it and pulling it sideways 24 away from the neck so that it breaks along one side and wipes the tapers as it is pulled from between them. The sleeve can be textured to facilitate the sleeve 14 wiping away debris. The sleeve can also be made of an absorbent material to facilitate absorbing fluid from the mating taper surfaces. Where the sleeve is designed to break during removal, it can be made of a non-stretching material.

In another embodiment, the sleeve 14 is pulled from the male 12 taper just as it is being inserted into the female taper 6 but without being pinched between the tapers. In this case the sleeve's 14 purpose is to protect the male taper 12 from contamination as it is inserted through the wound. Just prior to assembling the tapers, the sleeve 14 is pulled away to expose the clean male taper 12. The tapers are then impacted and locked together. To further protect the male taper 12 from contamination, the sleeve 14 can be made of a fluid impervious material such as a polymer film.

Figure 3:
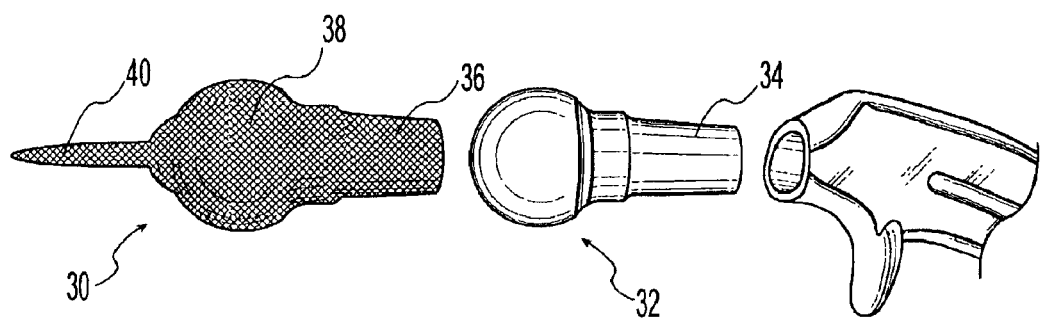
FIG. 3 is an exploded perspective view of an illustrative embodiment of a sleeve according to the present invention shown with modular implant components.
Figure 4:
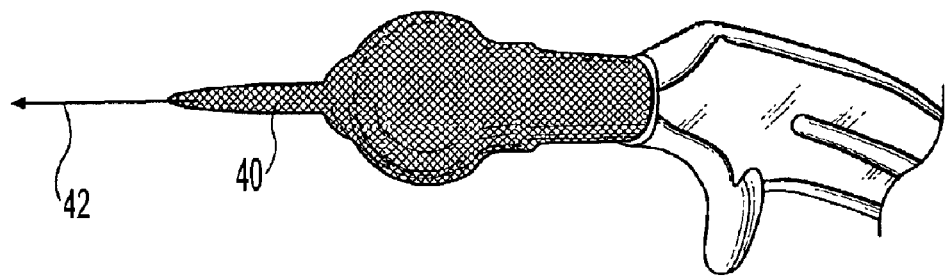
FIG. 4 is a perspective view of the sleeve of FIG. 3 assembled with the components of FIG. 3.

FIGS. 3 and 4 show another illustrative embodiment of a sleeve 30 for a head and neck 32 with a male taper 34. This sleeve 30 includes a portion 36 for covering the neck and a portion 38 for covering the head. A tab 40 extends from the sleeve 30 to facilitate its removal over 42 the head. The tab 40 can be a continuation of the material of the sleeve 30, or it can be a separate structure attached to the sleeve 30. For example, a knit sleeve could be made so that the knitting process is continued to form a knit extension from the sleeve. Alternatively, a yarn, bias tape or other material can be sewn or adhered to the sleeve. Similar tabs can be provided on sleeves made of non-woven or film-like materials.

Figure 5:
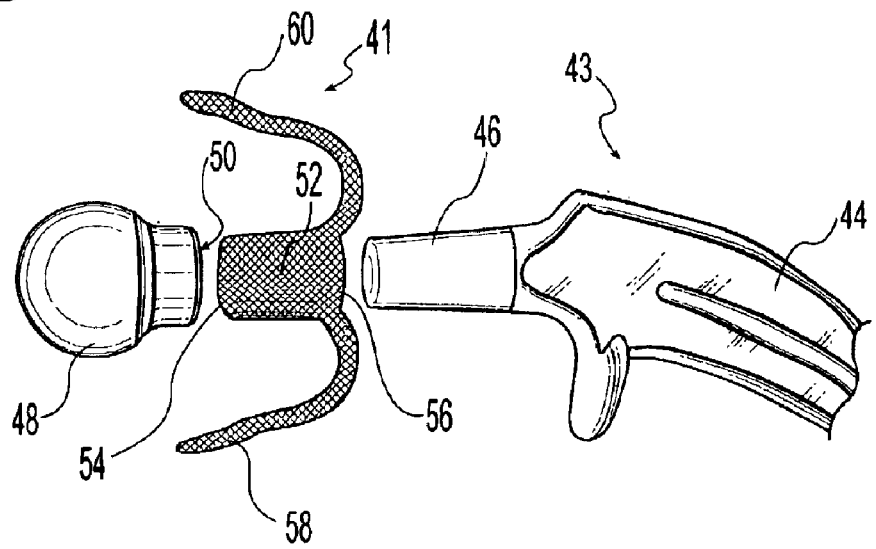
FIG. 5 is an exploded perspective view of an illustrative embodiment of a sleeve according to the present invention shown with modular implant components.
Figure 6:
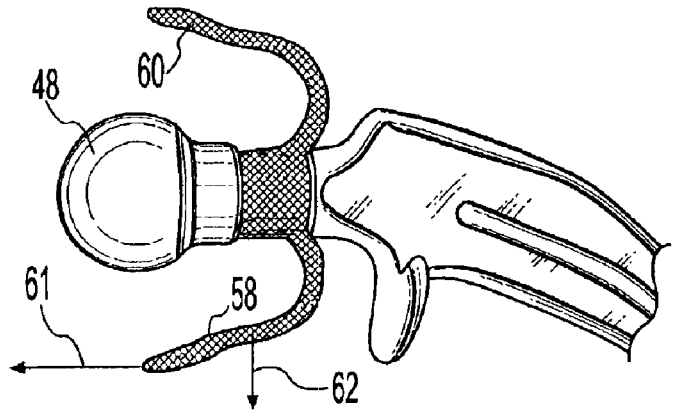
FIG. 6 is a perspective view of the sleeve of FIG. 5 assembled with the components of FIG. 5.

FIGS. 5 and 6 show another illustrative embodiment of a sleeve 41. This sleeve 41 is shown in conjunction with a stem 43 having a shaft 44 for insertion into the intramedullary canal of a femur and a neck with a male taper 46 having an external taper engaging surface for engaging an articulating head 48. The head includes a female taper 50 having an internal taper engaging surface for receiving the male taper 46 of the stem 43. The male taper 46 is received by the female taper 50 with their engaging surfaces in overlying engagement. The illustrative tapers 46, 50 form a locking junction that can be locked by impacting them together. The sleeve 41 includes a sidewall 52 forming a hollow cylinder with opposite open ends 54, 56. Tabs 58, 60 extend from one end 56 of the sleeve 41.

In use, the sleeve 41 functions similarly to the sleeve 14 of FIGS. 1 and 2. The partially covered taper 46 is loosely inserted into the female taper 50 with the sleeve 41 positioned between the overlying taper engaging surfaces. Prior to locking the tapers 46, 50 together, the sleeve is gripped by one end 56 and pulled from between the tapers to wipe the taper surfaces clean just before the tapers are locked together. The sleeve 41 can be gripped with a pair of forceps at one end 56. Alternatively, one or both of the tabs 58, 60 can be gripped and pulled to remove the sleeve. For a stretchable sleeve 41, it will turn wrong side out as it is pulled 61 from between the mating tapers and over the head 48. Alternatively the sleeve 41 can be made to break to allow it to be removed. The sleeve 41 can also be removed by gripping it and pulling it sideways 62 away from the neck so that it breaks along one side and wipes the tapers as it is pulled from between them. The various alternative materials applicable to the sleeve 14 of FIGS. 1 and 2 also apply to this sleeve 41.

Figure 7:
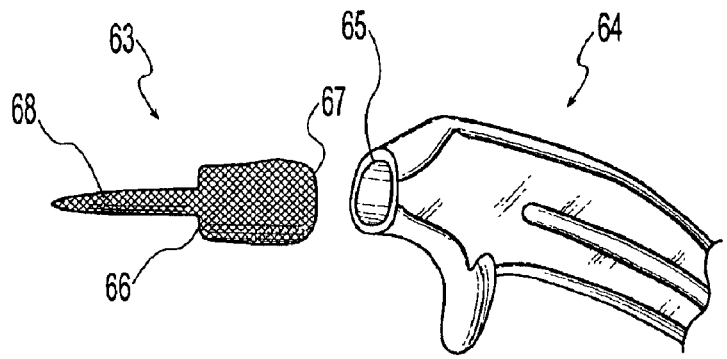
FIG. 7 is an exploded perspective view of an illustrative embodiment of a sleeve according to the present invention shown with an implant.
Figure 8:
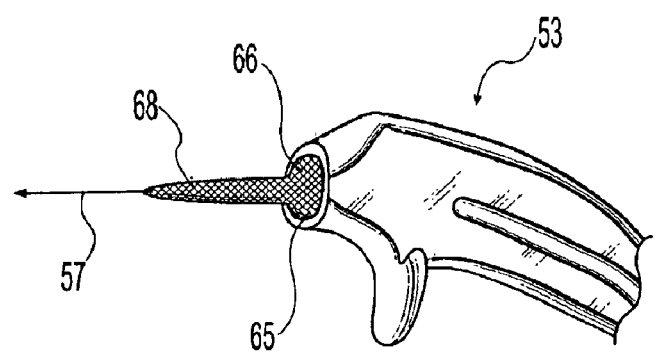
FIG. 8 is a perspective view of the sleeve of FIG. 7 assembled with the implant of FIG. 7.

FIGS. 7 and 8 show another illustrative embodiment of a sleeve 63 in use with a stem 64 having a female taper 65 with an internal taper engaging surface. This sleeve 63 comprises a body with opposite ends 66, 67 and fits within the female taper 65 to cover at least a portion of the internal taper engaging surface. In this embodiment, the sleeve 63 acts like a plug to protect the female taper 65. A tab 68 is attached to the sleeve 63 to facilitate its removal.

In use, the sleeve 63 is inserted into the female taper 65. The stem 64 is inserted through the wound into the femur. The sleeve is then gripped at one end 66 and removed 57 from the female taper 65 to expose and/or clean the taper for receiving a mating component such as a head and neck with a male taper. Tab 68 extends from the female taper 65 and may be gripped to facilitate removal of the sleeve 63.

Figure 9:
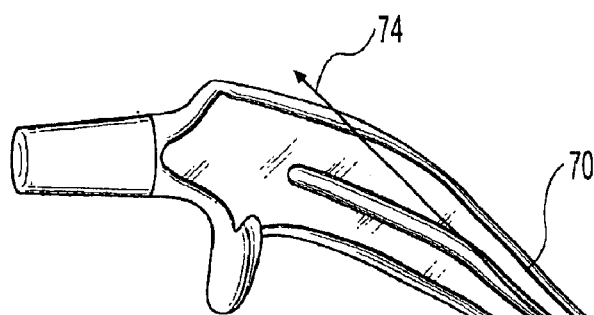
FIG. 9 is a perspective view of an illustrative embodiment of a sleeve according to the present invention shown on an implant.
Figure 9:
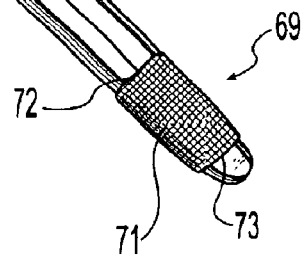

FIG. 9 shows another illustrative embodiment of a sleeve 69 for cleaning an implant stem 70. The sleeve 69 includes a sidewall 71 forming a hollow cylinder with opposite open ends 72, 73. The sleeve 69 can be made from a variety of materials and can include a tab to facilitate removal as described relative to the other embodiments. In the illustrative embodiment, it is shown as a woven or knit, absorbent fabric than can be fit over the stem 70 similar to a sock. The structure of the fabric allows it to stretch to fit over the stem in close-fitting relationship.

In use, the sleeve 69 is slipped onto the stem 70. The stem 70 is inserted through the wound and then the sleeve 69 is slid along 74 the stem 70 to clean the stem. One particular use for the sleeve 69 is to wipe the stem 70 as it is being inserted into a mass of cement placed in a bone to fix the stem 70 in place. In this case the sleeve 69 is placed on the stem, the stem inserted through the wound toward the cement, and as the stem enters the cement, the sleeve is slid along the stem to clean it just forward of the stem-cement interface.

Figure 10:
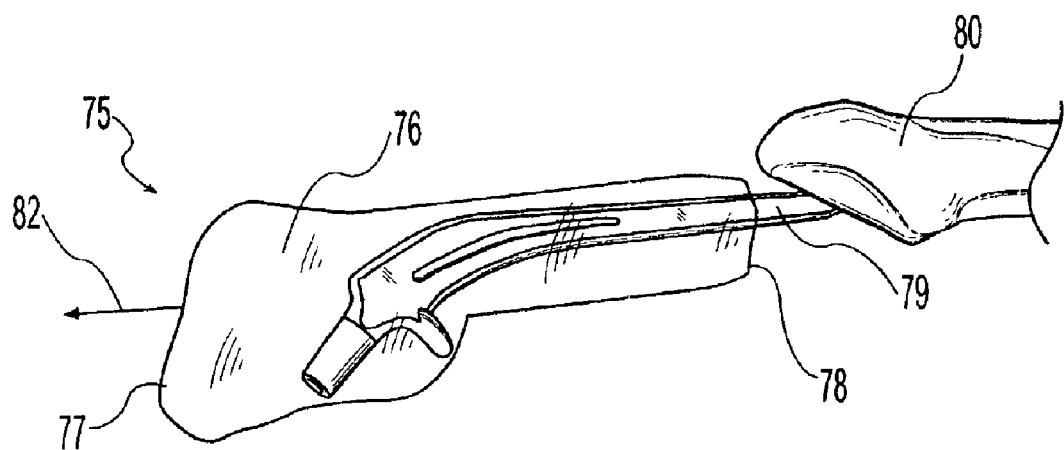
FIG. 10 is a side elevation view of an illustrative embodiment of a sleeve according to the present invention shown on an implant being inserted into a femur.
Figure 11:
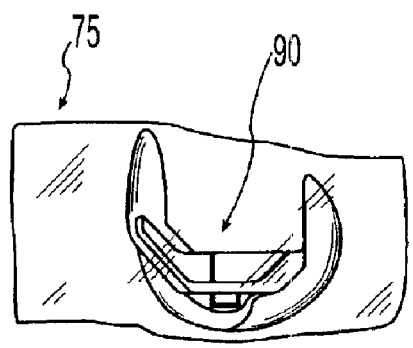
FIG. 11 is a side elevation view of an illustrative embodiment of a sleeve according to the present invention shown on an implant.

FIGS. 10 and 11 show an embodiment of a sleeve 75 comprising a protective film or bag 76. The sleeve 75 has ends 77, 78 that can be opened or closed. In the case where the ends are closed, they are made so that the sleeve 75 can be torn, or the implant pushed through the sleeve 75, to facilitate removal of the sleeve 75 from the implant. The sleeve 75 in FIG. 10 is shown with a hip stem 79. In use, the sleeve 75 is positioned around the stem to protect it from contamination during insertion through the wound toward a femur 80 containing a mass of cement for receiving the stem 79. The stem is inserted through the wound until it is adjacent the cement. As the stem 75 is inserted into the cement, the sleeve 75 is withdrawn 82 to progressively expose the clean stem 79.

The sleeve 75 in FIG. 11 is shown with a femoral knee joint component 90. In this case, the sleeve 75 can be used to protect cement that has been pre-applied to the component 90. In use, cement is applied to the component 90. The sleeve 75 is then positioned around the component to protect it from contamination during insertion through the wound toward a prepared distal end of a femur. The component is inserted through the wound until it is adjacent the receiving bone surface. As the component 90 is inserted into engagement with the bone, the sleeve 75 is withdrawn to expose the uncontaminated stem and pre-applied cement.

Another illustrative application of a sleeve 75 of this type is for use with an implant having a bone growth surface; e.g. fiber metal, trabecular metal, sintered beads, ceramics, plasma sprayed surfaces, grit blasted surfaces, and/or bone growth proteins applied to the surface, and the like. In this case, the sleeve would protect the surface from contamination from wound debris and fluids that might interfere with bone growth at the surface. Where materials such as bone growth proteins are applied to the surface, the sleeve would prevent the materials from being inadvertently removed as the surface passes through the wound. Some of the bone growth materials mentioned can be very rough and might tend to abrade and trap contaminates from the wound on their passing. Therefore, the sleeve 75 can be used to protect the wound from abrasion by such a rough implant surface. A sleeve for this purpose can take any of the forms previously described. A sleeve having a smooth and/or slippery surface can be used to ease the passage of the implant. A metal foil or a foil/polymer laminate can also be used and is tough and resistant to abrasion. A foil made of a biocompatible material such as titanium or stainless steel may be advantageously used.

The invention has been described in the context of a number of embodiments. These embodiments have been for illustration only and it is to be understood that the illustrated aspects of the invention are applicable to a variety of implants and not just those shown. The sleeve can be pre-applied and packaged with the implant or it can be applied at the time of surgery. Various other modifications may be made to these embodiments without departing from the spirit and scope of the invention defined by the appended claims.

What is claimed is:

1. A sleeve and implant combination comprising:
   a first implant component having a first engaging portion of a junction;
   a sleeve mounted on the first component and surrounding at least a portion of said first engaging portion;
   a second implant component having a second engaging portion of the junction, the second engaging portion being engageable with the first engaging portion to join the first and second implant components, the second engaging portion being engageable with the first engaging portion with at least a portion of the sleeve positioned between the first and second engaging portions within the junction, the sleeve being removable from the first engaging portion while the components are so engaged so that the sleeve wipes the engaging portions of the junction as it is removed.

2. The sleeve and implant combination of claim 1 wherein the sleeve comprises a material selected from the group consisting of a knitted material, a woven material, a non-woven fibrous material, a film, a foil, and a laminate of a foil and a polymer.

3. The sleeve and implant combination of claim 1 wherein the sleeve is made of a stretchable material so that it can be stretched to remove it from the first component.

4. The sleeve and implant combination of claim 3 wherein the sleeve is made of a knitted material.

5. The sleeve and implant combination of claim 1 wherein the sleeve has a textured surface for wiping at least one of the first and second engaging portions of the junction.

6. The sleeve and implant combination of claim 1 wherein the sleeve is made of an absorbent material.

7. The sleeve and implant combination of claim 1 wherein the sleeve is made of a polymer film.

8. The sleeve and implant combination of claim 1 wherein the sleeve is frangible so that it can be removed from the first component.

9. The sleeve and implant combination of claim 8 wherein the sleeve is frangible along a predetermined portion.

10. The sleeve and implant combination of claim 1 wherein the sleeve further comprises a tab extending from the sleeve to facilitate gripping the sleeve.

11. A sleeve for a femoral hip implant for insertion through a surgical wound and into a femur; the implant including a stem having a first end for insertion into the intramedullary canal of the femur, a second end with a taper junction, and a modular head member with a complimentary taper junction for engaging the stem taper junction; the sleeve comprising:
    a sleeve body for covering at least a portion of the implant as the implant is inserted through the surgical wound; and
    the sleeve is positioned between the complementary taper junctions as they are engaged so that as the sleeve is removed it wipes the complementary taper junctions.

12. The sleeve of claim 11 wherein the sleeve covers a portion of one of the head and stem complementary taper junctions.

13. The sleeve of claim 12 wherein the sleeve is fluid impervious to prevent contaminants from reaching the portion of the taper junction as the stem is inserted through the wound.

14. The sleeve of claim 11 wherein the sleeve includes a ring of material closely encircling a portion of the implant and being slidable along the implant to wipe the implant to clean the implant after it passes through said wound.

15. The sleeve of claim 11 wherein the sleeve includes a bag.

16. The sleeve of claim 15 wherein the sleeve is made of a polymer film.

17. A method of inserting a first implant component through a wound and into a surgical site, the method comprising the steps of:
    covering a portion of the first implant component with a flexible sleeve; placing cement at the surgical site;
    inserting the covered portion through the wound adjacent the cement;
    sliding the sleeve alone the first implant component to remove the sleeve simultaneously with inserting the portion into the cement; and
    seating the first implant component.

18. A method of inserting a first implant component through a wound and into a surgical site, the method comprising the steps of:

covering a portion of the first implant component with a flexible sleeve;

inserting the covered portion through the wound:

assembling the covered portion with a complementary mating portion of a second implant component, the first and second implant components forming a junction between them, at least a portion of the sleeve being positioned within the junction between the first and second components;

wiping at least a portion of the junction between the first and second implant components clean by pulling the sleeve from between them.

19. A method of inserting a first implant component through a wound and into a surgical site, the method comprising the steps of:

covering a portion of the first implant component with a flexible sleeve;

inserting the covered portion through the wound adjacent a bone;

sliding the sleeve alone the first implant component to remove the sleeve simultaneously with inserting the portion into the bone; and seating the first implant component.

20. A method of inserting a first implant component through a wound and into a surgical site, the method comprising the steps of:

covering a portion of the first implant component with a flexible sleeve;

inserting the covered portion through the wound;

sliding the sleeve alone the first implant component to remove the sleeve; and seating the first implant component, wherein covering the portion of the first implant component with a sleeve includes covering a male mating portion of the first implant component with a sleeve.

21. A method of inserting a first implant component through a wound and into a surgical site, the method comprising the steps of:

covering a portion of the first implant component with a flexible sleeve:

inserting the covered portion through the wound:

sliding the sleeve alone the first implant component to remove the sleeve: and seating the first implant component, wherein covering the portion of the first implant component with a sleeve includes covering a female mating portion of the first implant component with a sleeve.

* * * * *